United States Patent [19]

Ploem

[11] Patent Number: 5,549,439
[45] Date of Patent: Aug. 27, 1996

[54] COLLISION-FREE CONTROL SYSTEM FOR A MULTI-AXIALLY CONTROLLABLE MANIPULATOR

[76] Inventor: Sven Ploem, Kouwenberg 54, Cuijk, Netherlands, 5431 GZ

[21] Appl. No.: 290,791

[22] Filed: Oct. 7, 1994

[30] Foreign Application Priority Data

Feb. 17, 1992 [NL] Netherlands ............................ 9200286

[51] Int. Cl.⁶ ...................................................... H05G 1/00
[52] U.S. Cl. .............................. 414/680; 414/5; 378/204; 378/210
[58] Field of Search ................................ 414/5, 680, 685; 378/204, 208, 209, 210

[56] References Cited

U.S. PATENT DOCUMENTS

| | | |
|---|---|---|
| 3,414,136 | 12/1968 | Moore et al. . |
| 3,637,092 | 1/1972 | George et al. . |
| 3,893,573 | 7/1975 | Fletcher et al. . |
| 3,915,153 | 10/1975 | Quinn ........................................... 414/5 |
| 4,160,508 | 7/1979 | Salisbury, Jr. ................................ 414/4 |
| 4,168,782 | 9/1979 | Sturges, Jr. ................................... 414/4 |
| 4,604,016 | 8/1986 | Joyce ............................................ 414/5 |
| 4,639,172 | 1/1987 | Kishi et al. ................................ 364/474 |
| 5,020,089 | 5/1991 | Cromer et al. ............................ 378/209 |

FOREIGN PATENT DOCUMENTS 3732194  4/1988  Germany ................................ 378/204

*Primary Examiner*—Karen B. Merritt
*Assistant Examiner*—Gregory A. Morse
*Attorney, Agent, or Firm*—Weingarten, Schurgin, Gagnebin & Hayes

[57] ABSTRACT

A collision-free control system comprising a multi-axially controllable manipulator having interconnected supporting arms which are movable by way of actuators in such a way that a free end of the manipulator can be positioned spatially and moved into various positions. The actuators are controlled via a miniature model of the manipulator which is operated manually and is equipped with a series of position transducers which are capable of delivering control signals for commanding the actuators in such a way that the manipulator and the miniature model thereof always assume identical positions.

15 Claims, 1 Drawing Sheet

COLLISION-FREE CONTROL SYSTEM FOR A MULTI-AXIALLY CONTROLLABLE MANIPULATOR

FIELD OF INVENTION

The invention relates to a multi-axially controllable manipulator, essentially comprising interconnected supporting arms, which are movable by means of controllable displacement elements in such a way that the free end of the manipulator can be positioned spatially and moved into various positions, and also comprising control means for commanding actuators, which control means comprise a miniature model made substantially to scale of the manipulator, which miniature model can be operated manually and is equipped with a series of position transducers, which are capable of delivering control signals for commanding the actuators, in such a way that the manipulator and the miniature model thereof always assume identical positions.

BACKGROUND OF THE INVENTION

Multi-axially controllable manipulators are known and are generally described as robots in industrial applications. The free end of the robot, which can be equipped with, for example, a spraying head or welding head, travels along a more or less complex movement path, in which predetermined operations are performed in certain positions or while travelling along certain paths. The path to be travelled and the operations to be performed are fixed in a program, which is read out by the control means and converted into control signals for commanding actuators. Writing such a program is generally a complicated and time-consuming job and is therefore undertaken only in the case of repetitive movement patterns, as in the case of processing mass-produced products.

The programming work can be reduced by using so-called teach-in programming, in which the free end of the robot or manipulator travels along the desired movement path under manual control, which movement path is simultaneously recorded in a program, and which program can then be entered in the control means for commanding the actuators.

A multi-axially controllable manipulator of the above-described type for use in the case of non-repetitive movement patterns is known from U.S. Pat. No. 3,637,092. This known control system is generally described as a master-slave system, in which the slave—the manipulator—accurately follows the movements of the master—the miniature model of the manipulator—with little or no time delay.

The operator of the system has to maintain a close watch on the end of the manipulator in this case, in order to avoid collisions thereof with the object to be handled, for example a load to be gripped and then lifted.

In the case of a manipulator in the form of an X-ray apparatus, the free end of which is equipped with a C-shaped supporting arm which is provided at one end with an X-ray source and at the opposite end with an image sensor, the problem occurs that, although on the face of the X-ray apparatus can be moved into approximately the desired position relative to a patient to be examined with it, the correct, accurate relative position of X-ray apparatus and patient must be determined with the aid of the image which the image sensor displays on a screen set up for the operator, in this case the radiologist. The image displayed on the screen gives no information on the precise relative distance between the X-ray source and the patient to be examined, so that there is a risk that when the X-ray source is displaced "by feel", with the operator's eye directed at the screen, a "collision" between X-ray source and patient can occur, with the chance of serious injury for the patient.

The object of the invention is to provide a control system for a manipulator of the above-described type, which permits a rapid displacement of the free end thereof along a continuous movement path, in which collisions between the manipulator and the object to be examined or handled are ruled out with absolute certainty.

This object is achieved according to the invention through the fact that the control means comprise a miniature model of the object to be treated with the manipulator, while the scale ratio of the miniature model of the object to be treated is greater than the scale ratio of the miniature model of the manipulator, in order to form a collision-free safety zone in the immediate surroundings of the object to be treated.

By moving the miniature model of the manipulator by hand relative to the miniature model of the object to be treated, which is also made substantially to scale, while the movements—generally angular displacements—of the parts of the scale model are relayed in the ratio 1:1 to actuators of the manipulator by means of control signals generated by the position transducers, the free end of the manipulator can be moved into the correct position relative to the object to be examined, and the operator's attention need not be divided between the screen, on the one hand, and the actual movement of the free end of the manipulator, on the other. The movement of the manipulator can be controlled simultaneously over more than two axes.

Due to the fact that the miniature model of the object has a greater scale ratio than the scale ratio of the miniature model of the manipulator, collisions between a manipulator bearing an X-ray system and the patient to be examined therewith are avoided with absolute certainty.

If for example, 1:10 is selected as the scale ratio of the miniature model of the manipulator, and the miniature model of the object to be examined is 1:9, the operator can shift the free end of the manipulator scale model over a surface of the object miniature model, while the manipulator in this case remains at a distance from the object to be examined. With a safety zone thus created, the operator, in this case the radiologist, can shift the miniature model of the manipulator "by feel" and keep his/her attention fixed on the X-ray image, displayed on a screen, of the part of the patient's body to be examined.

According to an alternative embodiment of the invention, the object can also be achieved through the fact that the control means also comprise a miniature model of the object to be treated with the manipulator, the scale ratio of the miniature model of the manipulator being locally greater than that of the miniature model of the object through the local application of a material layer in order to form a safety zone.

Such a measure can be achieved by, for example, applying a layer of material of a certain thickness to the part of the miniature model of the manipulator corresponding to the X-ray source. The safety zone thus created also has the advantage that different objects of slightly different sizes can be examined with the same object miniature model.

It can be desirable for the manipulator to be brought into contact at several discrete points with the object to be examined or to be treated. At those points a "hole" must therefore be present in the safety zone. Such a "hole" is preferably obtained by making the object miniature model locally in a different scale ratio from the remainder of said miniature model, for example giving it a scale ratio which is the same as or smaller than that of the manipulator miniature model.

In the case of an object miniature model with scale ratio 1:9 and a manipulator miniature model with scale ratio 1:10, the object miniature model is also made at a certain point with a scale ratio 1:10, with the result that contact between manipulator and object is possible only at that point.

It may be desirable for the object to be examined or treated to be movably supported on a vertically adjustable and/or tiltable table which can be moved in the longitudinal direction.

This is, for example, the case during the X-ray examination of patients. In that case the miniature model of the object must rest on a miniature model of the supporting table, which is movable in the same way as the actual supporting table, and which is connected thereto in such a way that the miniature model and the supporting table always assume identical positions.

BRIEF DESCRIPTION OF THE DRAWING

An embodiment of the device according to the invention is explained in further detail with reference to FIG. 1.

DETAILED DESCRIPTION OF A PREFERRED EMBODIMENT

Figure 1:
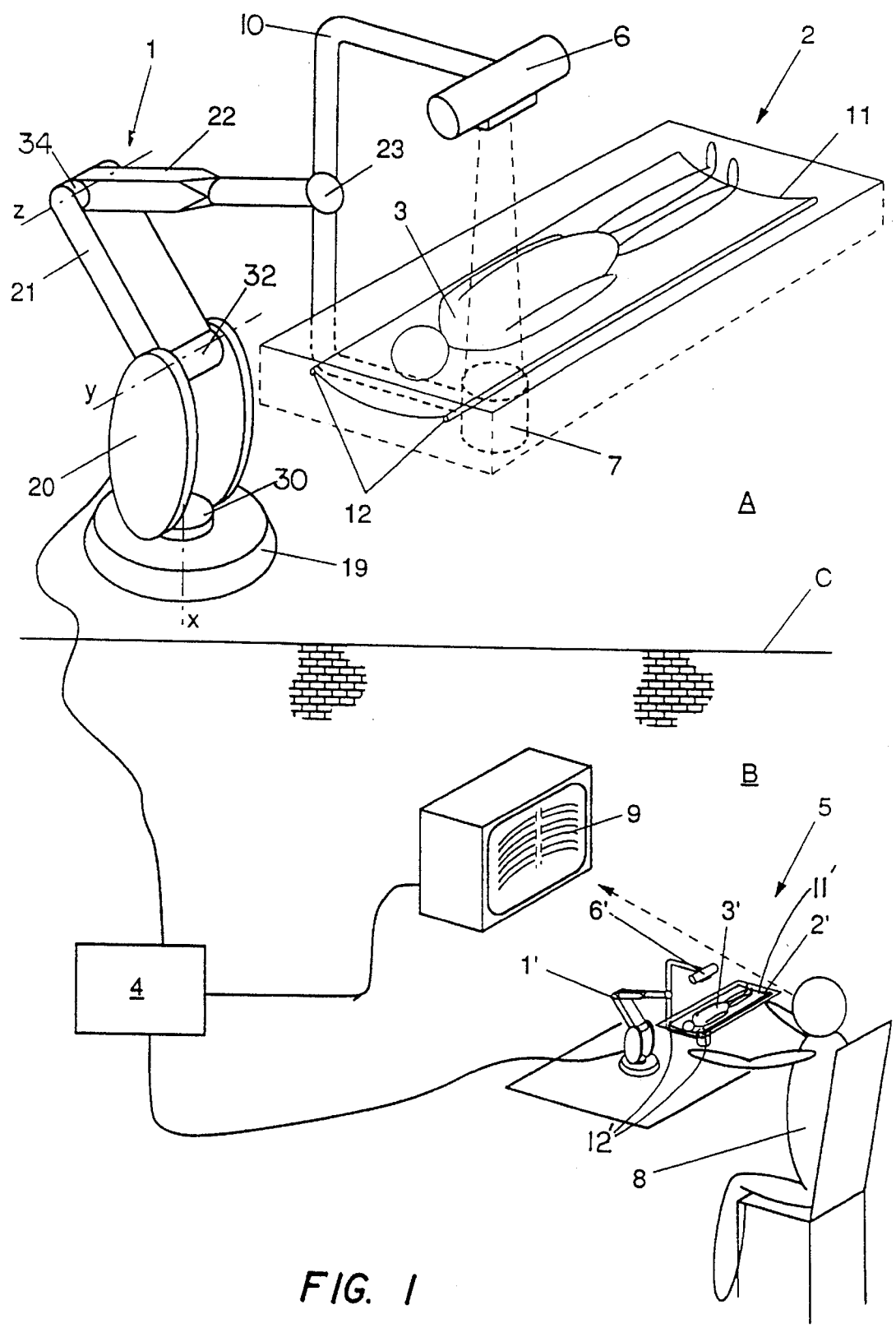
FIG. 1 shows diagrammatically a manipulator bearing an X-ray system, disposed in an area suitable for the purpose, while the control means therefor are accommodated in a screened-off area.

Disposed in an area A suitable for X-ray examination is a manipulator 1 bearing an X-ray system, and also a supporting table 2 for a patient 3. The manipulator 1 comprises a footplate 19, a stand 20 resting thereon and rotatable relative to the footplate 19 about a vertical axis X by means of a suitable actuator 30. A top arm 21 is hingedly connected to the stand 20 and can pivot by means of a suitable actuator 43 about a horizontal axis Y, while a bottom arm 22 is hingedly connected to the top arm 21 and can pivot by means of a suitable actuator 34 about a horizontal axis Z. The free end 23 of the bottom arm 22 is therefore spatially displaceable through rotation of the stand 20 and angular displacements of the top arm 21 relative to the stand 20 and of the bottom arm 22 relative to the top arm 21. Fixed at the free end 23 of the bottom arm 22 is a C-shaped bracket, one end of which is provided with an X-ray radiation source 6, while the other end of the bracket 10 bears an X-ray image sensor 7, the image sensor 7, of course, lying in the radiation beam of the X-ray source 6. The bracket 10 is suspended from the point 23, which can be called the wrist, in such a way than the bracket 10 can be pivoted about three axes which are at right angles to each other.

The supporting table 2 for the patient 3 can be made in such a way that it is vertically adjustable and can be shifted in the longitudinal direction, while the table 2 can also be tilted about an axis parallel to the short side thereof. The lying surface for the patient 3 on the table 2 is formed by an open-ended cloth strip 11, which is wound around two shafts 12 running in the lengthwise direction of the table 2. At least one of said shafts 12 can be driven in the peripheral direction in order to make the patient 3 assume a tilted position on the slightly sagging cloth strip 11, which is necessary or desirable in order to obtain a better X-ray picture of some parts of the body, for example in order to obtain a good distribution of contrast fluid in some organs of the patient.

The control means for the manipulator 1 and the supporting table 2 with the patient 3 lying thereon are situated in an area B which is screened off from the area A by a wall C. The control means comprise operating means 5, which comprise a miniature model 1' made substantially to scale of the manipulator 1 and a miniature model 3' of the patient 3, which miniature model 3' rests on a miniature model 2' made substantially to scale of the supporting table 2. Unlike the miniature model 1' of the manipulator 1 and the miniature model 2' of the supporting table 2, the miniature model 3' of the object to be examined or the patient 3 need not be an accurate scale model. This would also be extremely difficult to carry out during the examination of patients. The miniature model 3' of the patient 3 can be in the form of, for example, a Russian doll or even a block or cylinder, which on enlargement by the scale ratio factor at the position of the supporting table 2 creates a space in which the patient 3 can be accommodated safely, i.e. without the danger of collisions with the parts 6, 7, 10 of the manipulator 1. For the sake of simplicity, this block, cylinder or doll will be described below as miniature model 3' of the patient 3. It is important that this scale model 3' is fixed on the miniature model 2' of the supporting table 2 in a suitable manner, in order to prevent shifting of the model 3'.

The miniature model 1' of the manipulator 1 is provided with a number of position transducers, which can transmit the relative positions of the component parts of the miniature model 1 of the manipulator 1 and can deliver control signals corresponding thereto to a control unit 4, which is connected to the manipulator 1. On the basis of these control signals, the component parts of the manipulator 1 are moved into and held in the same position as that of the miniature model 1' of the manipulator 1.

A screen 9, for displaying thereon the X-ray images supplied by the image sensor 7, is also connected to the control unit 4.

The scale ratio of the miniature model 3' of the patient 3 differs from the scale ratio of the miniature model 1' of the manipulator 1. If the latter scale ratio is selected at, for example, 1:10, the scale ratio for the miniature model 3' of the patient 3 is, for example, 1:9. When an element 6' of the miniature model 1' corresponding to the X-ray source 6 of the manipulator 1 comes to rest against, for example, the chest of the miniature model 3' of the patient 3, the actual X-ray source 6 will remain at a distance from the chest of the patient 3. This different scale ratio means that a safety zone is created around the patient 3 and, for example, the X-ray source 6 of the manipulator 1 cannot enter said zone. Such a safety zone can also be obtained by giving the miniature model 3' of the patient 3 the same scale ratio as the miniature model 1' of the manipulator and applying a material layer of a certain thickness to, for example, the X-ray source 6' of the miniature model 1' of the manipulator 1. If the surface of this material layer is then resting on, for example, the chest of the miniature model 3' of the patient 3, the X-ray source 6 of the manipulator 1 will still be situated at a distance from the chest of the patient 3, this distance being determined by the thickness of the layer which is applied to the X-ray source 6' of the miniature model 1'. The same safety zone can be created by surrounding the miniature models 1' and 2' of the manipulator 1 and the supporting table 2 by walls of the area A made to scale and by also coating said walls with a layer of material, so that in the event of collision of parts of the miniature models 1' and 2' with the walls made to scale the actual manipulator 1 and the supporting table 2 still lie at some distance from the actual walls of the space A.

X-rays are made with the above-described device in the following way:

The patient 3 is placed on the supporting table 2. A radiologist 8 then places the miniature model 1' of the manipulator 1 by hand in approximately the correct position relative to the miniature model 2' of the patient 2. A fine adjustment is then sought, in the course of which the radiologist 8 looks at the screen 9 and displaces the miniature model 1' "by feel" in such a way that the optimum X-ray image is obtained. Thereafter, the miniature model 3' of the patient 3 can be tilted by driving a drivable shaft 12' of a cloth 11' of the miniature model 2', for the purpose of making other X-rays, the angular displacement of the shaft 12' being connected to the angular displacement of the rotary shaft 12 in such a way that patient 3 and miniature model 3' are tilted in the same position. If the supporting table 2 is provided with further displacement facilities, for example a displacement in the lengthwise direction, a vertical adjustment and a tilting facility about a short side of the supporting table 2, the miniature model 2' must also have the same displacement facilities, and the movements of the miniature model 2' are connected in the same way to the displacement elements of the supporting table 2 as is the case with the connection between the miniature model 1' and the manipulator 1.

In the case of such an object support 2, it is also provided with actuators and position transducers for adjustment and determination of the position respectively of the object support 2, while the miniature model 2' of the object support 2 is provided with position transducers which are connected only to the corresponding position transducers of the object support 2 by means of a comparison element, which in the presence of a difference signal between the position signals delivered by the two position transducers can deliver a control signal no an actuator belonging only to the particular position transducer of the object support 2, which actuator can be controlled in order to reduce the difference signal to zero.

When the manipulator 1 or the object support 2 makes movements which are not imposed by the control means 4, 5, for example as a result of faults, a safety mechanism goes into operation and, for example, switches off the power and fixes the manipulator 1 and the object support 2 in the current position by braking.

It is clear that the invention is not limited to the example of an embodiment described, and that various modifications are possible within the scope of the invention.

I claim:

1. A collision-free control system comprising a multi-axially controllable manipulator having interconnected supporting arms which are movable by means of controllable actuators in such a way that a free end of the manipulator can be positioned spatially and moved into various positions, and control means for commanding the actuators, said control means comprising a miniature model made substantially to scale of the manipulator, said miniature model being operated manually and being equipped with a series of position transducers which are capable of delivering control signals for commanding the actuators in such a way that the manipulator and the miniature model thereof always assume identical positions, said control means (4, 5) also comprising a miniature model (3') of an object (3) to be treated with the manipulator (1), wherein the scale ratio of the miniature model (3') of the object (3) to be treated is greater than the scale ratio of the miniature model (1') of the manipulator (1) in order to form a collision-free safety zone in the immediate surroundings of the object (3) to be treated.

2. The system according to claim 1, wherein the scale ratio of the miniature model (3') of the object (3) to be treated at one or more points is smaller than or equal to the scale ratio of the miniature model (1') of the manipulator (1) and at all other points is greater in order to form one or more holes in the safety zone.

3. The system according to claim 1, wherein the object (3) is placed on a multi-axially movable supporting surface (2), and wherein the control means (4, 5) comprise a miniature model (2') made substantially to scale of the object support (2), said model (2') being movable in the same way as the object support (2) and being connected thereto in such a way that the object support (2) and the miniature model (2') thereof always assume identical positions.

4. The system according to claim 3, wherein the object support is provided with actuators and position transducers for adjustment and determination of the position respectively of the object support (2), and wherein the miniature model (2') of the object support (2) is provided with position transducers which are connected only to the corresponding position transducers of the object support (2) by means of a comparison element, which in the presence of a difference signal between the position signals delivered by the two position transducers can deliver a control signal to an actuator belonging only to the particular position transducer of the object support (2), said actuator being controlled to reduce the difference signal to zero.

5. The system according to claim 4, wherein objects are placed in the movement area of the miniature models (1', 2') of the manipulator (1) and/or the object support (2) respectively in order to limit the movement area of the miniature models (1', 2'), and therefore of the manipulator (1) and/or the object support (2).

6. The system according to claim 1, wherein each position transducer of the miniature model (1') of the manipulator (1) is connected only to a corresponding position transducer of the manipulator (1) by means of a comparison element, which in the presence of a difference signal between the position signals delivered by the two position transducers can deliver a control signal to an actuator belonging only to the particular position transducer of the manipulator, said actuator being controlled to reduce the difference signal to zero.

7. The system according to claim 1, wherein objects are placed in the movement area of the miniature models (1', 2') of the manipulator (1) and/or the object support (2) respectively in order to limit the movement area of the miniature models (1', 2'), and therefore of the manipulator (1) and/or the object support (2).

8. An X-ray apparatus comprising a manipulator (1) equipped with an X-ray source (6) and an image sensor (7), and an object support (2) on which an object (3) to be examined is placeable, the manipulator (1) being movable by means of controllable actuators in such a way that a free end (23) of the manipulator (1) can be positioned spatially and moved into various positions, the object support (2) being movable by means of controllable actuators in such a way that the object (3) can be moved into various positions, the apparatus further comprising an image screen (9) for displaying an image detected by the image sensor (7) and control means situated in an area (B) screened off from the X-ray source (6), the control means comprising a miniature model (1', 2') made substantially to scale of the manipulator (1) and of the object support (2'), said miniature models (1', 2') being operated manually and being equipped with a series of position transducers which are capable of delivering control signals for commanding the actuators in such a way that the manipulator (1) and the object support (2) and the respective miniature models (1', 2') thereof always assume identical positions, the apparatus being capable of being operated with a collision-free safety zone in the immediate surroundings of the object to be examined.

9. The X-ray apparatus according to claim 8, wherein the control means also comprise a miniature model (3') of the object (3) to be treated.

10. The X-ray apparatus according to claim 9, wherein the miniature model (3') of the object (3) is fixed on, or integrated with, the miniature model (2') of the object support (2).

11. A collision-free control system comprising a multi-axially controllable manipulator having interconnected supporting arms which are movable by means of controllable actuators in such a way that a free end of the manipulator can be positioned spatially and moved into various positions, and control means for commanding the actuators, said control means comprising a miniature model made substantially to scale of the manipulator, said miniature model being operated manually and being equipped with a series of position transducers which are capable of delivering control signals for commanding the actuators in such a way that the manipulator and the miniature model thereof always assume identical positions, said control means (4, 5) also comprising a miniature model (3') of an object (3) to be treated with the manipulator (1), wherein the scale ratio of the miniature model (1') of the manipulator (1) is locally greater than that of the miniature model (3') of the object (3) to be treated due to a material layer on the miniature model (1') of the manipulator (1) in order to form a safety zone.

12. The system according to claim 1, wherein the scale ratio of the miniature model (3') of the object (3) at one or more points is smaller than or equal to the scale ratio of the miniature model (1') of the manipulator (1) and at all other points is greater in order to form one or more holes in the safety zone.

13. The system according to claim 12, wherein the object is placed on a multi-axially movable supporting surface, and wherein the control means (4, 5) comprise a miniature model (2') made substantially to scale of the object support (2), said model (2') being movable in the same way as the object support (2) and being connected thereto in such a way that object support (2) and the miniature model (2') thereof always assume identical positions.

14. The system according to claim 11, wherein each position transducer of the miniature model (1') of the manipulator (1) is connected only to a corresponding position transducer of the manipulator (1) by means of a comparison element, which in the presence of a difference signal between the position signals delivered by the two position transducers can deliver a control signal to an actuator belonging only to the particular position transducer of the manipulator, said actuator being controlled to reduce the difference signal to zero.

15. The system according to claim 11, wherein objects are placed in the movement area of the miniature models (1', 2') of the manipulator (1) and/or the object support (2) respectively in order to limit the movement area of the miniature models (1', 2'), and therefore of the manipulator (1) and/or the object support (2).

\* \* \* \* \*

UNITED STATES PATENT AND TRADEMARK OFFICE
CERTIFICATE OF CORRECTION

PATENT NO. : 5,549,439
DATED : August 27, 1996
INVENTOR(S) : Sven Ploem

It is certified that error appears in the above-indentified patent and that said Letters Patent is hereby corrected as shown below:

Column 2, between lines 3 and 4, Heading is missing and should read --SUMMARY OF THE INVENTION--.

Column 3, line 39, "43" should read --34--.

Column 5, line 33, "no an" should read --to an--.

Column 7, line 30, claim 12, "according to claim 1," should read --according to claim 11,--.

Signed and Sealed this

Twenty-fifth Day of August, 1998

Attest:

BRUCE LEHMAN

*Attesting Officer*  *Commissioner of Patents and Trademarks*